United States Patent
Simard et al.

(10) Patent No.: US 8,865,175 B2
(45) Date of Patent: *Oct. 21, 2014

(54) INCREASING ANTI-IL-1α ANTIBODIES IN A SUBJECT

(75) Inventors: John Simard, Austin, TX (US); Klaus Bendtzen, Lynge (DK)

(73) Assignee: XBiotech, Inc., Vancouver (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/473,939

(22) Filed: May 17, 2012

(65) Prior Publication Data

US 2012/0231012 A1 Sep. 13, 2012

Related U.S. Application Data

(63) Continuation of application No. 11/997,496, filed as application No. PCT/IB2006/002038 on Jul. 26, 2007, now Pat. No. 8,187,817.

(60) Provisional application No. 60/704,450, filed on Aug. 2, 2005.

(51) Int. Cl.
 A61K 39/395 (2006.01)
 G01N 33/564 (2006.01)
 C07K 16/24 (2006.01)

(52) U.S. Cl.
 CPC ................................. *G01N 33/564* (2013.01)
 USPC ................... 424/145.1; 424/158.1; 530/387.1; 530/388.23; 530/388.7; 530/389.2

(58) Field of Classification Search
 None
 See application file for complete search history.

(56) References Cited

U.S. PATENT DOCUMENTS

| | | | |
|---|---|---|---|
| 5,959,085 A * | 9/1999 | Garrone et al. ............ | 530/387.3 |
| 7,718,674 B2 | 5/2010 | Aberg | |
| 8,187,817 B2 * | 5/2012 | Simard et al. .................. | 435/7.1 |
| 2003/0175832 A1 | 9/2003 | Marton | |
| 2005/0276807 A1 | 12/2005 | Skurkovich | |
| 2006/0127407 A1 | 6/2006 | Chen | |
| 2009/0258070 A1 | 10/2009 | Burnier | |
| 2009/0291081 A1 | 11/2009 | Hsieh | |
| 2010/0047239 A1 | 2/2010 | Wu | |
| 2010/0221179 A1 | 9/2010 | Hsieh | |

FOREIGN PATENT DOCUMENTS

| EP | 0267611 | 5/1993 |
|---|---|---|
| WO | 2010087972 | 8/2010 |

OTHER PUBLICATIONS

Ross et al, Blood, 1997, vol. 90, No. 6, pp. 2376-2380.*
"Autoantibody" and "monoclonal antibody" definitions from Stedman Online Medical dictionary; downloaded Mar. 5, 2013; 2 pages.*

Mizutani, H.: "Endogenous neutralizing anti-Il-1alpha antibodies in inflammatory skin diseases: possible natural inhibitor for over expressed epidermal IL-1," 1999, Journal of Dermatological Science, vol. 20:63-71.
Zhu, Y. et al., "The clinical study about interleukin-1 and tumor necrosis factor alpha in hepatocirrhosis," Chinese Journal of Clinical Hepatology, 2001, vol. 17, Issue 4: 233-234.
Skrzeczynska, J. et al., "CD14+CD16+ Monocytes in the Course of Sepsis in Neonates and Small Children: Monitoring and Functional Studies," Scandinavian Journal of Immunology, 2002, vol. 55:629-638.
Barkley, D.E.H. et al: "Cells with dendritic morphology and bright interleukin-1alpha staining circulate in the blood of patients with rheumatoid arthritis," Clin.Exp.Immmunol., 1990, vol. 80:25-31.
Yanni, G. et al: "Intramuscular gold decreases cytokine expression and macrophage numbers In the rheumatoid synovial membrane," Annals of the Rheumatic Diseases, 1994, vol. 53:315-322.
Dekker, S.K. et al: "Characterization of interleukin-1alpha-induced melanoma cell motility: inhibition by type I and type II receptor-blocking monoclonal antibodies," Melanoma Research, 1997, vol. 7:223-230.
Kleiman, et al: "Invasion assays," Current Protocols in Cell Biology, 2001, 12.2.1-12.2.5.
Sawai, H. et al: "Interleukin-1alpha enhances the aggressive behavior of pancreatic cancer cells by regulating the alpha 6 beta I-integrin and urokinase plasminogen activator receptor expression," MC Cell Biology, 2006:1-13.
Lewis, Anne M. et al: "Interleukin-I and cancer progression: the emerging role of interleukin-I receptor antagonist as a novel therapeutic agent in cancer treatment," Journal of Translational Medicine, 2006, vol. 4:1-12.
Li, X. et al: "Interleukin-1alpha up-regulation in vivo by a potent carcinogen 7, 12-Dimethylbenz(a)anthracene (DMB) and control of DMBA-induced inflammatory responses," Cancer Res, 2002, vol. 62:417-423.
Nozaki, S. et al: "Cancer Cell-Derived Interleukin 1alpha contributes to autocrine and paracrine induction of pro-metastatic genes in breast cancer," Biochemical and Biophysical Research Communications, 2000, vol. 275:60-62.
Voronov, E. et al: "IL-1 is required for tumor invasiveness and angiogenesis," PNAS, 2003, vol. 100, No. 5:2645-2650.
Uefuji, K. et al: "Increased expression of interleukin-1alpha and cyclooxygenase-2 in human gastric cancer: a possible role in tumor progression," 2005, Anticancer Research, vol. 25:3225-3230.
Shreeniwas, R. et al: "Hypoxia-mediated induction of endothelial cell interleukin-1alpha: an autocrine mechanism promoting expression of leukocyte adhesion molecules on the vessel surface," 1992, J. Clin. Invest., vol. 90:2333-2339.

(Continued)

*Primary Examiner* — Joanne Hama
*Assistant Examiner* — Fozia Hamud
(74) *Attorney, Agent, or Firm* — Stanley A. Kim

(57) ABSTRACT

Method of detecting individuals at risk for atherosclerosis and related vascular diseases involving the detection of IL-1α autoantibodies, as well as therapeutic methods to prevent or treat atherosclerosis and related vascular disease by administering a pharmaceutical composition comprising IL-1α autantibodies.

2 Claims, No Drawings

(56) References Cited

OTHER PUBLICATIONS

Kaji, Mitsuhito et al, E-selectin expression induced by pancreas-carcinoma-derived interleukin-1alpha results in enhanced adhesion of pancreas-carcinoma cells to endothelial cells, Intl Journal of Cancer, 1995, vol. 60, Issue 5:712-717.

Fukumoto, Y. et al., Inflammatory Cytokines Cause Coronary Arteriosclerosis-Like Changes and Alterations in the Smooth-Muscle Phenotypes in Pigs, Journal of Cardiovascular Pharmacology, 1997, vol. 29:222-231.

Chamberlain, R.S. et al., Innovations and strategies for the development of anticancer vaccines, Exp. Opin. Pharmacother., 2000, vol. 1(4)603-614.

Jefferis, Roy: "Antibody therapeutics: isotype and glycoform selection," Expert Opin. Biol. Ther. (2007) 7 (9):1401-1413.

Salfeld, J.G.: "Isotype selection in antibody engineering," Nature Biotechnology (2007), vol. 25, No. 12:1369-1372.

Pascual, V. et al: "Role of interleukin-1 (IL-1) in the pathogenesis of systemic onset juvenile idiopathic arthritis and clinical response to IL-1 blockade," The Journal of Experimental Medicine (2005), vol. 201, No. 9:1479-1486.

Buchan, G. et al: "Interleukin-1 and tumour necrosis factor mRNA expression in rheumatoid arthritis: prolonged production of IL-1alpha," Clin. Exp. Immunol. (1988), vol. 73:449-455.

Hata, H. et al: "Distinct contribution of IL-6, TNF-alpha, IL-1, and IL-10 to T cell-mediated spontaneous autoimmune arthritis in mice," The Journal of Clinical Investigation (2004), vol. 114, No. 4: 582-588.

Chen, Z. et al: "Effects of interleukin-1alpha, interleukin-1 receptor antagonist, and neutralizing antibody on proinflammatory cytokine expression by human squamous cell carcinoma lines," Cancer Research (1998), vol. 58:3668-3676.

\* cited by examiner

INCREASING ANTI-IL-1α ANTIBODIES IN A SUBJECT

CROSS-REFERENCE

This application is a continuation of U.S. patent application Ser. No. 11/997,496 filed on Oct. 20, 2008 (now U.S. Pat. No. 8,187,817), which is a national stage application of international patent application PCT/IB2006/002038 filed on Jul. 26, 2007, claiming priority from U.S. patent application No. 60/704,450 filed on Aug. 2, 2005. These applications are incorporated herein by reference in their entirety.

FIELD OF THE INVENTION

The invention relates to diagnosis, treatment, and prevention of vascular disorders. More specifically, the invention relates to use of IL-1α autoantibodies to diagnose, treat, and prevent vascular disorders.

BACKGROUND OF THE INVENTION

For decades atherosclerosis has been investigated for its role in at least three diseases, heart disease (HD), peripheral arterial disease (PAD) and cerebrovascular disease (CD). The pathologic processes in these disease categories are similar, and atherosclerosis is now considered a systemic disease irrespective of which vascular bed is affected. Consequently, the social burden of atherosclerosis is enormous: in 2002 there were an estimated 71,100,000 persons in the US affected with heart disease, resulting in 947,428 deaths at a cost of US $393.5 billion dollars. There are 5,400,000 Americans living with the effects of stroke, costing an estimated $56.8 in healthcare in 2005. The global burden of atherosclerosis is expected to rise.

Atherosclerosis is a systemic disease. In many patients it is both insidious and affects more than one vascular bed. Early detection of atherosclerosis or identification of patients susceptible to developing atherosclerosis is crucial to preventing morbidity and mortality. There is, therefore, a need in the art to identify methods of identifying patients at risk for developing atherosclerosis as well as methods of treating patients already affected with an atherosclerosis-related disorder.

DETAILED DESCRIPTION OF THE INVENTION

The present invention relates to the observation that a high titer of IL-1α autoantibodies in humans reduces the risk of ischemic heart disease or its progression to coronary heart disease. The present invention provides a powerful means of detecting an individual at risk for developing atherosclerosis or an atherosclerosis-related disorder by determining the individual's IL-1α autoantibody titer. The invention also provides methods of using IL-1α autoantibodies to reduce risk, progression, or symptoms of vascular disease (e.g., coronary heart disease, peripheral arterial disease, and cerebrovascular disease).

IL-1α is released in sufficient quantities to induce high-affinity, high titer, neutralizing antibody responses in as many as 50% of patients analyzed, primarily in older men. Hansen et al., *Eur. J. Clin. Invest.* 24, 212-18, 1994. Furthermore, the ability of individuals to develop IL-1α autoantibodies provides a protective effect against some unknown role of IL-1α in the progression of pathological inflammatory processes in the arterial wall (atherosclerosis).

The correlation between risk of vascular disorders and IL-1α autoantibody titers is surprising because IL-lot is believed to exert its biological actions primarily at an intracellular level, as an autocrine substance, in the close vicinity of the cell producing IL-1α as a membrane-associated molecule, or as a strictly paracrine substance. Moreover, there is no current mechanism to explain the role of IL-1α in the progression of atherosclerosis. Thus, it is unexpected that an antibody targeting IL-1α would be of therapeutic value in the treatment or prevention of vascular diseases.

IL-1α Autoantibodies

"IL-1α autoantibodies" according to the invention include full-length antibodies isolated from B cells (including activated and/or immortalized B cells), blood, serum, or plasma; functional antibody fragments containing IL-1α binding sites of full-length IL-1α autoantibodies (e.g., F(ab)'$_2$ fragments, F(ab)' fragments, Fab fragments, double-stranded Fv fragments, and single-chain antibodies); recombinant immunoglobulin molecules produced by expressing cDNA derived from B cells or by expressing synthetic nucleotide sequences which encode the immunoglobulin molecules; monoclonal autoantibodies (produced as described below); and synthetic IL-1α autoantibodies (produced as described below). An IL-1α autoantibody typically is an IgG molecule, particularly an IgG$_4$ molecule (Garrone et al., *Mol. Immunol.* 33, 649-58, 1996), but can be an IgM, IgE, IgA, or IgD molecule. IL-1α autoantibodies also include any of the molecules described above which are coupled to another molecule (such as a receptor, ligand, enzyme, toxin, carrier, etc.) and autoantibodies made by combining the variable portions of an autoantibody of one isotype with the constant regions of another isotype.

IL-1α autoantibodies preferably bind with high affinity to IL-1α. High affinity IL-1α autoantibodies typically have an equilibrium affinity constant ($K_a$, or the reciprocal of $K_D$) for IL-1α binding of between $10^{14}$ M$^{-1}$ and $5 \times 10^{-7}$ M$^{-1}$ (e.g., $5 \times 10^7$, $10^{13}$, $5 \times 10^{-8}$, $10^{-12}$, $5 \times 10^8$, $10^9$, $5 \times 10^9$, $10^{10}$, $5 \times 10^{10}$, $10^{11}$, $5 \times 10^{11}$, $10^{12}$, $5 \times 10^{12}$, $10^{13}$, or $5 \times 10^{13}$ M$^{-1}$). Specific binding of an IL-1α autoantibody to IL-1α can be determined using any appropriate method including, for example, technologies such as real-time Bimolecular Interaction Analysis (BIA) (Sjolander & Urbaniczky, *Anal. Chem.* 63, 2338-45, 1991, and Szabo et al., *Curr. Opin. Struct. Biol.* 5, 699-705, 1995). $K_a$ can be calculated from a Scatchard plot of specific binding data, as is known in the art. See also U.S. Pat. No. 5,959,085.

IL-1α autoantibodies of the invention preferably neutralize IL-1α bioactivity (e.g., IL-1α-induced IL-2 secretion) in vitro and in vivo. More preferably, IL-1α autoantibodies reduce or eliminate binding of IL-1α to its receptor. Neutralizing activity and receptor binding activity can be assayed as described in Satoh et al., *Immunopharmacology* 27, 107-18, 1994.

The methods and compositions described below encompass human IL-1α autoantibodies as well as IL-1α autoantibodies of other mammals including, but not limited to, other primates (e.g., gorillas, chimpanzees, baboons, squirrel monkeys), companion animals (e.g., cats, rabbits, dogs, horses), farm animals (e.g., cows, sheep, swine, goats, horses), and research animals (e.g., cats, dogs, guinea pigs, rabbits, sheep, goats, swine, chimpanzees, and baboons).

Methods of Obtaining IL-1α Autoantibodies

IL-1α autoantibodies can be obtained by a variety of methods. In some embodiments, preparations of polyclonal IL-1α autoantibodies are obtained from B cells, blood, plasma, or serum, either from a single individual or from pooled samples from 2 or more individuals. Sources of B cells include peripheral blood, tonsils, adenoids, and spleen. See U.S. Pat. No. 5,959,085. The individual(s) can be healthy or can have an autoimmune disease, particularly an autoimmune disease in which IL-1α autoantibodies are overproduced. These diseases include, e.g., Schnitzler's syndrome (Saurat et al., *J. Allergy Clin. Immunol.* 88, 244-56, 1991), autoimmune blistering disorders (e.g., pemphigus/phemphigoid) (Garrone et al., 1996), and chronic inflammatory arthritis (Garrone et al., 1996). Blood donors which are positive for the presence of circulating IL-1α autoantibodies can be identified using known methods, such as ELISA, radioimmunoprecipitation, Western blot, etc. See, e.g., Satoh et al., 1994; Saurat et al., 1991; Svenson et al., *J. Clin. Invest.* 92, 2533-39, 1993; Bendtzen et al., *Mol. Biotechnol.* 14, 251-61, 2000; Svenson et al., *Scand. J. Immunol.* 29, 489-92, 1989; Svenson et al., *Scand J. Immunol.* 32, 695-701, 1990; Svenson et al., *J. Clin. Invest.* 92, 2533-39, 1993; and Svenson et al., *Cytokine* 4, 125-33, 1992. In some embodiments, plasma is obtained using plasmapheresis or apheresis.

In some embodiments, donor serum is screened using an IL-1α enzyme-linked immunoadsorbant assay (ELISA). Because very low free IL-1α in the serum will correlate with the presence of neutralizing autoantibodies against IL-1α, the test allows for very quick screening and short-listing of donor serum for those with the high potential for providing appropriate neutralizing antibodies. This approach can simplify the initial screening process and reduce development time. IL-1α assay kits are available, for example, from Abazyme LLC; Alpco Diagnostics; Antigenix America Inc.; Autogen Bioclear UK Ltd; Bender MedSystems; Biosource International; BioVision; Cayman Chemical; Cell Sciences; CHEMICON; CytoLab Ltd., Endogen; GE Healthcare (formerly Amersham Biosciences); Leinco Technologies, Inc.; PeproTech; and R&D Systems.

IL-1α autoantibodies can be purified from individual or pooled blood, plasma, or serum using methods well known in the art, such as ultrafiltration, dialysis, washing after immobilization on a non-specific protein support, or affinity chromatography on a specific protein support. See US 2005/0147603. Human IL-1α autoantibodies can be purified from commercial preparations of human IgG (e.g., SANDOGLOBULIN® (Sandoz, Copenhagen, Denmark), GAMMGARD® (Baxter, Allerød, Denmark), or NORDIMMUNO (Novo Nordisk, Bagsvaerd, Denmark). See Ross et al., *J Interferon Res.* 14, 159-60, 1994; Svenson et al., *J. Clin. Invest.* 92, 2533-39, 1993. Affinity purification of IL-1α autoantibodies is described, for example, in Satoh et al., 1994.

In some embodiments, pools of plasma or serum collected from, e.g., 100 donors can be tested for binding of radiolabeled IL-1α to IgG using Protein G affinity chromatography. A suitable radiolabel is $^{125}$I. The radiolabeled tracer is observed for binding to IgG in pools, and recovery of added natural IL-1α to these pools can be assessed using an IL-1α ELISA. Plasma or serum of donors contributing to a positive pool can be reassessed individually and saturable binding of IL-1α to IgG in 10% of the plasma (judged by saturation binding of radiolabeled IL-1α to IgG) can be determined. For example, dilutions of donor plasma highly positive for IL-1α autoantibodies can be incubated with $^{125}$I-labeled IL-1α (3,500 cpm) in a final volume of 200 µl. IgG-bound tracer can be assessed by Protein G affinity chromatography. IgG-bound and free $^{125}$I-labeled IL-1α can be separated by secondary antibody precipitation. Average dissociation or affinity constants and maximal IL-1α IgG-binding capacities can be calculated using Scatchard plots.

Donors with highly positive sera, i.e., those harboring IL-1α autoantibodies with picomolar avidity at plasma antibody concentrations between 0.1 nM and 35 nM, can be used to harvest IL-1α autoantibody-producing B lymphocytes from peripheral blood. However, useful IL-1α autoantibodies may exhibit a range of avidity, from femtomolar to nanomolar avidity, which may be considered useful for therapeutics, depending on the target and desired pharmacokinetics of the antibody therapeutic. Plasma concentrations of IL-1α autoantibodies may range significantly and, depending on the sensitivity and efficiency of cloning or enrichment, may be in the range of 0.1 picomolar to 0.1 nanomolar, or conversely may be in high concentrations in the range 35 nM to 3500 nm, as is the case for plasma B cell malignancies. Peripheral blood lymphocytes which produce IL-1α autoantibodies can be stimulated to grow in culture and, therefore, can be immortalized using methodologies well known in the art using, for example, a virus (e.g., Epstein Barr virus, EBV), a chemical agent, or a nucleic acid (such as an oncogene). The immortalized cells can then be cloned using known methods to provide a reliable source of large amounts of human IL-1α autoantibodies.

In some embodiments, B lymphocytes from blood samples of appropriate donors are immortalized in bull culture with EBV in the presence of irradiated mononuclear cells and a toll-like receptor agonist (such as a CpG oligonucleotide), which acts as a polyclonal activator of memory B cells and increases their susceptibility to EBV infection. Immortalized B lymphocytes are then selected for IgG-positive memory B lymphocytes by a combination of magnetic and fluorescence-activated cell sorting. Supernatants from cultures containing 10 IgG-positive memory B cells can be analyzed after 12-14 days for the presence of specific IL-1α autoantibodies. Positive cultures are re-plated, and limiting dilution is used to isolate individual immortalized B lymphocyte clones with appropriate production of IL-1α autoantibodies. See, for example, WO 91/09115 and U.S. Pat. No. 5,959,085.

In other embodiments, isolated lymphocytes are used to produce hybridomas as is well known in the art. (See, e.g., Methods in Enzymology, Vol. 121, Sections I and II, 1986; Garrone et al., 1996). Hybridomas which produce IL-1α autoantibodies can be propagated in vitro as is known in the art to provide a constant source of the autoantibodies. Alternatively, hybridoma cells can be injected intraperitoneally into mice, which will then produce tumors. These tumors are accompanied by the production of ascites fluid which contains the desired monoclonal autoantibodies. The monoclonal autoantibodies can be recovered from the ascites fluid by conventional methods such as ultrafiltration, ultracentrifugation, dialysis, and immunoaffinity chromatography.

RNA can be obtained from an immortalized B cell clone or a hybridoma clone and used as a template for an amplification reaction (e.g., PCR) to obtain cDNA encoding for an IL-1α autoantibody. See U.S. Pat. No. 5,959,085. cDNA encoding a full-length IL-a autoantibody or a functional fragment thereof can be included in an expression vector and used to express the IL-1α autoantibody in prokaryotic or eukaryotic host cells using recombinant DNA methodologies well known in the art. See, e.g., Garrone et al., 1996. The host cells can then be used to propagate the IL-1α autoantibody. Alternatively, any particular IL-1α autoantibody can be isolated and its amino acid sequence determined by known methods. Nucleic acid molecules which encode the amino acid sequence can be synthesized and used in an expression vector to produce cloned IL-1α autoantibodies. If desired, the original heavy chain constant region of an IL-1α autoantibody can be replaced by a constant region of a different isotype (e.g., $IgG_1$, $IgG_2$, $IgG_3$, $IgG_4$, IgA, IgD, IgM, or IgE). See U.S. Pat. No. 5,959,085.

IL-1α autoantibodies can be chemically synthesized using techniques known in the art. See, e.g., Merrifield, *J. Am.*

Chem. Soc. 85, 2149-54, 1963; Roberge et al., *Science* 269, 202-04, 1995. Protein synthesis can be performed using manual techniques or by automation. Automated synthesis can be achieved, for example, using Applied Biosystems 431A Peptide Synthesizer (Perkin Elmer). Optionally, fragments of an IL-1α autoantibody can be separately synthesized and combined using chemical methods to produce a full-length molecule.

IL-1α autoantibodies can be obtained by screening antibody libraries, such as HuCAL® (Knappik et al., *J. Mol. Biol.* 296, 57-86, 2000), scFv phage display libraries (e.g., Pharmacia Recombinant Phage Antibody System, catalog no. 27-9400-01; and the Stratagene SURZAP™ phage display kit, catalog no. 240612), and the like. See WO 92/18619; WO 92/20791; WO 93/01288; WO 92/01047; WO 92/09690; Fuchs et al., *Bio/Technology* 9, 1370-72, 1991; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J. 12:725-734; Hawkins et al. (1992) J Mol Biol 226:889-896; Clackson et al. (1991) Nature 352:624-628; Gram et al. (1992) PNAS 89:357&3580 Garrad et al. (1991) Bio/Technology 9:1373-1377; Hoogenboom et al. (1991) Nuc Acid Res 19:4133-4137; and Barbas et al. (1991) PNAS 88:7978-7982.

If desired, modifications can be made to IL-1α autoantibodies to enhance their binding affinity for IL-1α. See, e.g., U.S. Pat. No. 6,914,128.

Screening Methods

According to the invention, a low titer of IL-1α autoantibodies or the presence of low affinity human anti-IL-1α autoantibodies indicates a likelihood that the individual will progress to an atherosclerosis-related disorder or that the severity of the individual's atherosclerosis-related disorder will increase. An individual has a "low titer" of IL-1α autoantibodies if a positive response in an immunoassay (e.g., a radioimmunoassay, ELISA, or Western blot) is detected at a dilution of the individual's serum of no more than about 1:100 (e.g., a dilution of 1:1, 1:10, 1:50, or 1:100). An individual has a "high titer" of IL-1α autoantibodies if a positive response in an immunoassay can still be detected at a dilution of more than about 1:100 (e.g., 1:1000, 1:10,000, 1:100,000, etc.). Low affinity IL-1α autoantibodies typically have a K for IL-1α binding of between 10 $M^{-1}$ and $10^7 M^{-1}$ (e.g., 10, $5\times10^2$, $10^3$, $5\times10^3$, $10^4$, $5\times10^4$, $10^5$, $5\times10^5$, $10^6$, $5\times10^6$, and $10^7 M^{-1}$).

A test biological sample (comprising, e.g., blood, plasma, serum) from an individual can be assayed to determine a test titer of IL-1α autoantibodies. The individual can be healthy, or apparently healthy, or can be known to have an atherosclerosis-related disorder. The atherosclerosis-related disorder can be, for example, cerebral vascular disease, peripheral vascular disease, ischemic heart disease, or coronary artery disease.

Any method known in the art can be used to detect IL-1α autoantibodies in the individual's test biological sample. These methods include, but are not limited to, binding to radiolabeled IL-1α, ELISA, competitive binding of IL-1α to its receptor, FITC-labeled IL-1α using flow cytometry, Western blot, etc. See, e.g., Bendtzen et al., *Mol. Biotechnol.* 14, 251-61, 2000; Ross et al., *Blood* 90, 2376-80, 1997; Hansen et al., *Immunol. Lett.* 30, 133, 1991; Svenson et al., *Scand. J. Immunol.* 29, 489-92, 1989; Svenson et al., *Scand J. Immunol.* 32, 695-701, 1990; Svenson et al., *Cytokine* 4, 125-33, 1992; Saurat et al., *J. Allergy Clin Immunol.* 88, 244-56, 1991. Radioimmunoassays, such as those described in Bendtzen et al., *Mol. Biotechnol.* 14, 251-61, 2000, are preferred. Titers of autoantibodies to IL-1α in a test biological sample can be calculated using standard methods known in the art. Assays can be carried out either qualitatively or quantitatively. Alternatively, using FITC-labeled IL-1α for identification of B lymphocytes expressing an IL-1α autoantibody, IL-1α-specific B lymphocyte frequency can be correlated with serum IL-1α levels and thus be an indicator of the risk of developing atherosclerosis or a related disorder.

Pharmaceutical Compositions and Therapeutic Methods

Pharmaceutical compositions of the invention comprise high affinity IL-1α autoantibodies as defined above. The IL-1α autoantibodies can be derived from a single source (for example, a single individual, a clone of an immortalized B cell clone, or a single hybridoma) or from two or more such sources, including two or more preparations of monoclonal IL-1α autoantibodies or a mixture of monoclonal and polyclonal IL-1α autoantibodies. Pharmaceutical compositions are non-pyrogenic.

Pharmaceutically Acceptable Vehicles

"Pharmaceutically acceptable vehicles" include any and all solvents, dispersion media, coatings, antibacterial and antifungal agents, isotonic and absorption delaying agents, and the like which are physiologically compatible. Examples of pharmaceutically acceptable vehicles include one or more of water, saline, phosphate buffered saline, dextrose, glycerol, ethanol, etc., as well as combinations thereof. In cases one or more isotonic agents are included, such as sugars, polyalcohols such as mannitol, sorbitol, or sodium chloride. Pharmaceutically acceptable vehicles may further comprise minor amounts of auxiliary substances such as wetting or emulsifying agents, preservatives, or buffers, which enhance the shelf life or effectiveness of the IL-1α autoantibodies.

Pharmaceutical compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application.

For example, IL-1α autoantibodies can be lyophilized into a highly pure crystalline form. The final product can be supplied as a sterile, lyophilized powder suitable for reconstitution and parenteral infusion. Lyophilized powder can be contained in sterile vials, each containing between, e.g., 1-1000 mg of IL-1α autoantibodies. Each vial can contain additional non-medical ingredients, such as one or more of the following; sucrose, polysorbate 80, monobasic sodium phosphate, monohydrate, polyethylene glycol and dibasic sodium phosphate and dihydrate.

In some embodiments, IL-1α autoantibodies in a vial can be reconstituted immediately prior to use with, for example, 1-30 mL of Sterile Water for Injection, USP, with a resulting pH of approximately 7.2. Preservatives can be included. If the product does not contain preservatives, the product typically is used immediately after reconstitution and not re-entered or stored. The total dose of the reconstituted product can be further diluted to 50-500 mL with 0.9% Sodium Chloride Injection, USP. The infusion concentration can range between 0.04 mg/mL and 40 mg/mL. Infusion can begin, for example, within about 1-4 hours after reconstitution. Preferably, the infusion solution is administered over a period of about 2 hours using an infusion set with an in-line, sterile, non-pyrogenic, low-protein-binding filter (pore size of 1.2 μm or less).

In other embodiments, Il-1α autoantibodies are formulated into a pharmaceutical composition suitable for parenteral administration, for example, as an injectable solution. IL-1α autoantibodies can be in a liquid or lyophilized dosage form, for example, in a flint or amber vial, ampule, or pre-filled syringe. Suitable buffers include L-histidine, sodium succinate, sodium citrate, sodium phosphate, and potassium phosphate. Sodium chloride can be used to modify the toxicity of the solution at a concentration of 0-300 mM (e.g., 150 mM for a liquid dosage form). Cryoprotectants can be included for a lyophilized dosage form (e.g., 0-10% sucrose, trehalose, or lactose). Bulking agents, such as mannitol, also can be included for a lyophilized dosage form. Stabilizers such as L-methionine can be used in both liquid and lyophilized dosage forms. Surfactants, e.g., polysorbate 20 and BRIJ surfactants, can be included.

Pharmaceutical compositions of the invention can be used to treat atherosclerosis-related disorders, including ischemic heart disease, coronary artery disease, peripheral arterial disease, and cerebrovascular disease. Individuals preferably are treated with pharmaceutical preparations comprising autoantibodies of the same species (i.e., humans are treated with human IL-1α autoantibodies). A therapeutically effective amount of a pharmaceutical composition according to the invention can be administered to an individual having symptoms of one or more of these disorders or can be administered prophylactically to individuals at risk for developing one or more of these disorders. A "therapeutically effective amount" is an amount which reduces the amount of free IL-1α in the individual's serum or which raises an individual's IL-1α autoantibody titer by at least two-fold. Preferably, the individual's symptoms of an atherosclerosis-related disorder are reduced (e.g., cramping in hips, thighs or calves; angina).

Pharmaceutical compositions of the invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In some embodiments, the Il-1α autoantibodies can be prepared with a carrier that will protect the autoantibodies against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Both the dose and the administration schedule of pharmaceutical preparations of the invention will vary depending on the individual's risk of developing an atherosclerosis-related disorder, the symptoms and severity of an individual's disease, and the individual's species. Typical doses of IL-1α autoantibodies are in the range of 0.001 µg to 400 mg/kg (e.g., 0.001 µg, 0.01 µg, 0.1 µg, 0.5 µg, 1.0 µg, 10 µg, 100 µg, 1 mg, 2 mg, 5 mg, 10 mg, 15 mg, 20 mg, 25 mg, 50 mg, 75 mg, 100 mg, 150 mg, 200 mg, 250 mg, 300 mg, 350 mg, or 400 mg). The dose can be administered, for example, daily for 4 days, once weekly, twice monthly, monthly, once every 12 weeks, once every 24 weeks, or once every 90 days.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Correlation of Ischemic Heart Disease with Il-1α Autoantibody Titer

Serum samples from men enrolled in the Copenhagen Male Study (CMS; Gyntelberg, Dan Med Bull 1973; 20:1-4) were examined for IL-1α autoantibody titer. The men ranged in age from 53 to 75 years (mean=63). The results are shown in Table 1.

TABLE 1

| quintile (no. individuals) | aAb-IL-1α titer | Percent with ischemic heart disease at 10 year follow-up |
|---|---|---|
| 1 (132) | 0 | 20.5% |
| 2-4 (379) | Low | 18.7% |
| 5 (137) | High | 12.2% |

As indicated in Table 1, at the 10-year follow-up of these patients there was a decreased incidence of ischemic heart disease in those individuals having high IL-1α autoantibody titers.

EXAMPLE 2

Autoantibodies to Il-1α in Patients with Ischemic Heart Disease

Sera from 20 patients were studied within 3 days of coronary artery bypass surgery and compared with 20 age-matched males without signs of ischemic heart disease. The results are shown in Table 2.

|  | Males with ischemic heart disease | Healthy males | Total |
|---|---|---|---|
| +IL-1α autoantibodies | 0 | 12 | 12 |
| −IL-1α autoantibodies | 20 | 8 | 28 |
|  | 20 | 20 | 40 |

P < 0.0001 (Fisher's exact test, two-sided)

EXAMPLE 3

Isolation and Stimulation of Mononuclear Cells

This example describes one suitable method for isolating and stimulating mononuclear cells. Mononuclear cells (MNC) from healthy blood donors is obtained using donors negative for IL-1α autoantibodies. MNC are purified from buffy coats by centrifugation on LYMPHOPREP™ (Nycomed). Cells are washed in RPMI 1640 containing 2 mM L-glutamine (Sigma, St. Louis, USA), 25 µg/ml gentamycin (GIBCO® BRL, Life Technologies, Paisley, Scotland) and 5% normal human AB serum. Native IL-1α (nIL-1α) is generated by stimulating MNC at 37° C. in 5% $CO_2$ humidified air in the presence of 100 µg/ml *E. coli* LPS (Difco Laboratories, Detroit, USA). After 12 h, the supernatant is harvested and stored at −20° C. until use.

Protein G Affinity Chromatography

Affinity chromatography of 100 µl plasma samples is carried out at 4° C. using columns containing 2000 µl Protein G Sepharose 4 Fast Flow (Amersham Biosciences). Phosphate-buffered saline pH 7.4 (PBS) supplemented with 0.1% (v/v)

Triton X-100 and 0.1% (w/v) gelatin (Sigma) is used as running buffer. Bound material is eluted with 0.1 M glycine/HCl, pH 2.4.

Specificity Analyses

Antibody specificity analyses are carried out with different preparations of natural and recombinant IL-1α together with radiolabeled rIL-1α. Plasma samples which are positive for anti-IL-1α are diluted to bind approximately 60% of a total of 15 ng/200 μl IL-1α, including both unlabeled IL-1α and tracer IL-1α (15 pg/200 μl $^{125}$I-labeled IL-1α). The mixture of plasma, tracer, and competitor is pre-incubated for 1 h at 37° C. and then subjected to affinity chromatography on Protein G. Fractions corresponding to IgG-bound and free tracer are counted in a gamma counter (1470 WIZARD™ gamma counter, Wallac, Finland). In addition, free IL-1α is measured by ELISA.

Screening Plasma Samples by RIA and ELISA

Plasma samples are collected from individual blood donors according to appropriate protocols and quality control of blood components. Samples are initially mini-pool screened for anti-IL-1α. Mini-pools of 90 plasma samples are adjusted to 25% (v/v) in PBS supplemented with 0.1% (v/v) Triton X-100 (Sigma), 0.1% (w/v) gelatin (Sigma) and 2 mM EDTA (Bie & Berntsen, Rodovre, Denmark) (PBS+), and 3,500 cpm $^{125}$I-labeled IL-1α is added; there is a final volume of 200 μl. After incubation for 20 h at 4° C., fractions representing IgG-bound tracer and free tracer are separated by Protein G and counted. In addition, anti-IL-1α binding activity is addressed with regard to natural IL-1α. This can be done by measuring recovery of 1 ng/ml natural IL-1α in the presence of 25% plasma pools in an IL-1α ELISA.

IL-1α ELISA

This sandwich ELISA is based on specific polyclonal rabbit anti-human IL-1α antibodies. It has been validated thoroughly with respect to interference from natural human IL-1α antibodies. See Hansen et al., Scand. J. Immunol. 1991. 33: 777-781; Hansen et al., Cytokine 1993.5: 72-80:

IMMUNO® MAXISORP® plates (Nunc, Roskilde, Denmark) are coated with Protein A affinity-purified rabbit anti-human IL-1α IgG. Non-attached sites are blocked with PBS containing 4% (w/v) skimmed milk powder, 1% (w/v) human serum albumin (HSA) (SSI, Copenhagen, Denmark) and 0.005% (v/v) TWEEN® 20 (Merck). The wells are washed with PBS/0.005% TWEEN® 20 after each of the following steps: 1) 100 μl analyte incubated for 18 h at 4° C.; 2) 100 μl biotinylated rabbit anti-human IL-1A IgG (2 μg/ml) in PBS/0.005% (v/v), TWEEN® 20/0.5% (w/v) HSA, incubated for 2 h at 20° C.; 3) 100 μl streptavidin-peroxidase (0.1 μg/ml; Kirkegaard & Perry Laboratories, Gaithersburg, USA) in PBS/0.005% (v/v) Tween 20/0.5% (w/v) HSA, incubated for 45 min at 20° C. Enzyme activities are quantitated using 1,2-phenylenediamine dihydrochloride (DalcoCytomation). The working range of the ELISA is from 150 pg/ml to 5,000 pg/ml. The inter- and intra-assay coefficients of variation are maintained below 15%.

HS IL-1α ELISA

Plasma IL-1α levels are quantified using the IL-1A Quantikine High Sensitivity ELISA (R&D Systems, Minneapolis, Minn.). According to the manufacturer's validation and instructions, this ELISA detects IL-1α bound to both sIL-1αR and IL-1α autoantibodies.

Secondary Antibody Precipitation and Scatchard Plots

The binding characteristics of IL1α autoantibodies in selected antibody-positive plasma samples are assessed as previously described (Hansen et al., Eur. J. Immunol. 1995. 25: 348-354). Appropriately diluted plasma samples are mixed with $^{125}$I-labeled IL-1α ranging from 50,000 cpm to 700 cpm in PBS+ in a final volume of 100 μl. After incubation at 4° C. for 20 h, 200 μl rabbit anti-human IgG (A424; DakoCytomation) is added to precipitate more than 95% of the IgG. After incubation for 1 h at 4° C., three volumes of PBS is added. The samples are centrifuged immediately for 20 min (3000×g at 4° C.) after which the amounts of IL-1α in the pellets (IgG-bound) and the supernatants (free) are counted. Affinities of IL-1α autoantibodies for IL-1α binding are calculated using Scatchard plots.

What is claimed is:

1. A method of raising the serum titer of anti-IL-1α antibodies in an individual previously determined to have a low serum titer of IL-1α autoantibodies, the method comprising the step of: administering to the individual previously determined to have a low serum titer of IL-1α autoantibodies a pharmaceutical composition which consists essentially of: antibodies that target IL-1α and a pharmaceutically acceptable vehicle.

2. The method of claim 1, wherein the antibodies that target IL-1α have a $K_a$ for IL-1α of between $10^7$ and $10^{14}$ M$^{-1}$.

* * * * *